United States Patent
Nishijima et al.

(10) Patent No.: US 7,709,671 B2
(45) Date of Patent: May 4, 2010

(54) DEODORIZED POLYETHER-MODIFIED POLYSILOXANE COMPOSITION, METHOD FOR PRODUCING THE SAME, AND COSMETIC CONTAINING THE SAME

(75) Inventors: Kazuhiro Nishijima, Yokohama (JP); Seiki Tamura, Yokohama (JP); Hiroaki Shoji, Tokyo (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 888 days.

(21) Appl. No.: 10/499,828

(22) PCT Filed: Nov. 17, 2003

(86) PCT No.: PCT/JP03/14573

§ 371 (c)(1),
(2), (4) Date: Aug. 30, 2005

(87) PCT Pub. No.: WO2004/046226

PCT Pub. Date: Jun. 3, 2004

(65) Prior Publication Data

US 2006/0018935 A1    Jan. 26, 2006

(30) Foreign Application Priority Data

Nov. 18, 2002    (JP)    ............... 2002-333423

(51) Int. Cl.
*C07F 7/18*    (2006.01)
(52) U.S. Cl. ................ 556/450; 514/722; 514/723
(58) Field of Classification Search ................ 514/723, 514/722; 556/450
See application file for complete search history.

(56) References Cited

U.S. PATENT DOCUMENTS

| | | | |
|---|---|---|---|
| 4,222,952 A | 9/1980 | Vick | |
| 4,661,612 A | 4/1987 | George et al. | |
| 5,225,509 A | 7/1993 | Heinrich et al. | |

FOREIGN PATENT DOCUMENTS

| | | |
|---|---|---|
| JP | 59-4446 | 1/1984 |
| JP | 8-231707 | 9/1996 |
| JP | 9-202829 | 8/1997 |
| JP | 11-60723 | 3/1999 |
| JP | 2000-327785 | 11/2000 |
| JP | 2003-96192 | 4/2003 |
| JP | 2003-105088 | 4/2003 |
| JP | 2003-292607 | 10/2003 |
| JP | 2003-342363 | 12/2003 |
| JP | 2004-2506 | 1/2004 |

OTHER PUBLICATIONS

Patent Abstracts of Japan, Publication No. 2-302438, dated Dec. 14, 1990./Cited in the International Search Report./Discussed in the specification.
Patent Abstracts of Japan, Publication No. 7-330907, dated Dec. 19, 1995./ Cited in the International Search Report./Discussed in the specification.
Patent Abstracts of Japan, Publication No. 9-165315, dated Jun. 24, 1997./Cited in the International Search Report./Discussed in the specification.
Patent Abstracts of Japan, Publication No. 9-165318, dated Jun. 24, 1997./Cited in the International Search Report./Discussed in the specification.
Cover page of WO 02/055588 A1, dated Jul. 18, 2002./Cited in the International Search Report./Discussed in the specification.

*Primary Examiner*—Elvis O Price
(74) *Attorney, Agent, or Firm*—Edwards Angell Palmer & Dodge LLP

(57) ABSTRACT

The deodorized, polyether-modified polysiloxane composition not producing a substance giving off a foul odor, while being produced or stored, which results from hydrolysis, oxidation or the like of a by-product or unreacted material and temporarily stable, a method for producing the same, and a cosmetic containing the same, wherein a polyether-modified polysiloxane composition, synthesized by hydrosilylation in which a polyoxyalkylene having the carbon-carbon double bond at the terminal is reacted with an organohydrogen polysiloxane, is refined by treatment in the presence of a solid acid.

13 Claims, No Drawings

DEODORIZED POLYETHER-MODIFIED POLYSILOXANE COMPOSITION, METHOD FOR PRODUCING THE SAME, AND COSMETIC CONTAINING THE SAME

BACKGROUND OF THE INVENTION

1. Field of the Invention

The present invention relates to a deodorized, polyether-modified polysiloxane composition, method for producing the same and cosmetic containing the same, more particularly a deodorized, polyether-modified polysiloxane composition not producing a substance giving off a foul odor, while being produced or stored, which results from hydrolysis, oxidation or the like of a by-product or unreacted material and temporarily stable, and method for producing the same and cosmetic containing the same.

2. Description of the Prior Art

A polyether-modified polysiloxane is traditionally synthesized by hydrosilylation in which a polysiloxane having hydrosilyl group is reacted with a polyoxyalkylene having an unsaturated bond.

The polyether-modified polysiloxane, however, involves a disadvantage of giving off a foul odor with the lapse of time, making itself difficult to be used for cosmetics, e.g., those for the hair or skin.

This disadvantage was considered to result from deterioration of the polyether-modified polysiloxane by oxidation which occurs with the lapse of time to form aldehyde. However, another cause is reported. For example, JP-A-2-302438 discusses that a foul odor results from an unreacted, propenyl-etherified polyoxyalkylene (refer to the claims or the like). More specifically, part of an allyl-etherified polyoxyalkylene is transformed into a propenyl-etherified polyoxyalkylene because of its double bond migrating inwards in the presence of a platinum catalyst while the polysiloxane composition modified with a polyether is being produced. As a result, it remains unreacted with an organohydrogen polysiloxane to be left in the polysiloxane composition modified with a polyether, and is decomposed with the lapse of time into a ketone or aldehyde to give off a foul odor. The patent document also discloses that the composition can be effectively deodorized by hydrolysis in the presence of an acid. This deodorizing approach will be effective for removal of the unsaturated group, when the allyl group in the residual polyoxyalkylene is totally transformed into propenyl group. In actuality, however, the allyl-etherified polyoxyalkylene undergoing no rearrangement remains to some extent to reduce the deodorizing effect, because the isomerization in the presence of a platinum catalyst reaches an equilibrium. In other words, the approach disclosed by the above patent document involves a problem of insufficient acid strength for hydrolysis of an allyl-etherified polyoxyalkylene.

Hydrolysis of an allyl-etherified polyoxyalkylene in the presence of a stronger acid is not adequate, because of the possible scission of the carbon-oxygen bond in the polyoxyalkylene or silicon-oxygen bond in the polysiloxane.

Moreover, the hydrolysis needs excessive quantities of water and acid in order to proceed quantitatively, which introduce greater complexity into the post-treatment. Therefore, the above deodorization approach is not ideal. Still more, the foul odor results not only from the carbon-carbon double bond but also from unstable oxides or the like difficult to identify. This is another problem involved in the above approach.

In consideration of the disadvantages involved in the deodorization based on the hydrolysis in the presence of an acid, varied solutions have been proposed to control formation of odorous substances by hydrolysis, oxidation or the like of polyether-modified polysiloxane. For example, U.S. Pat. No. 5,225,509 discloses a method for deodorizing a polyoxyalkylene polysiloxane by hydrogenation under the conditions of temperature: 20 to 200° C., pressure: 1 to 100 bars and reaction time: 0.5 to 10 hours in the presence of a hydrogenation catalyst (refer to the claims or the like). JP-A-7-330907, 9-165315 and 9-165318 disclose that a polyether-modified polysiloxane composition, synthesized by hydrosilylation in which a polyoxyalkylene having the carbon-carbon double bond at the terminal is reacted with an organohydrogen polysiloxane, can be temporarily stable without giving off a foul odor, when hydrogenated (refer to the claims or the like).

However, the composition treated only by hydrogenation may still contain an aldehyde condensate, e.g., acetal, which can be transformed into the aldehyde in an aqueous solution to cause foul odor. This is because hydrogenation alone cannot sufficiently treat an aldehyde condensate, which lacks an unsaturated bond, to remove odorous substances.

In consideration of the above problems, WO-02/055588, for example, proposes a deodorized, modified silicone compound having a degree of unsaturation and aldehyde formed each controlled at a specific level or less, and cosmetic containing the same, where the modified silicone compound is refined by (A) hydrogenation of the residual unsaturated bond and subsequent decomposition of an aldehyde condensate in an acid-containing, aqueous solution kept at a pH of 7 or less, or (B) decomposition of a propenyl-etherified product in an acid-containing, aqueous solution kept at a pH of 7 or less and subsequent hydrogenation of the aldehyde formed and residual unsaturated bond (refer to claims or the like).

The above proposal, however, needs treatment in an acid-containing, aqueous solution kept at a pH of 7 or less as the essential step. Therefore, the acidic substance in the aqueous solution is dissolved and hence remains in the system. As a result, the acid treatment should be generally followed by a neutralization step, and the salt formed by the neutralization also partly remains in the system. Thus, the above proposal involves the problems that the acid substance and salt by the neutralization remain in the system. In particular, a polyether-modified polysiloxane is more hydrophilic than a dimethyl polysiloxane, and allows the acidic substance and salt by neutralization to remain in the system to a higher content. These residual substances cause another problem of retarding the hydrogenation step, when it follows the neutralization step.

Moreover, a polyether-modified polysiloxane containing trace quantities of the acidic substance and salt by neutralization also involves a problem of causing a foul smell of the system with the lapse of time, when it comprises water and a polyhydric alcohol, conceivably resulting from, e.g., the residual substances themselves or a decomposition product thereof, or a decomposition product of the polyether-modified polysiloxane.

SUMMARY OF THE INVENTION

In consideration of the above problems, it is an object of the present invention to provide a deodorized, polyether-modified polysiloxane composition not producing a substance giving off a foul odor, while being produced or stored, which results from hydrolysis, oxidation or the like of a by-product or unreacted material, and temporarily stable. It is another object of the present invention to provide a method for producing the same composition. It is still another object of the present invention to provide a cosmetic containing the same composition.

The inventors of the present invention have found, after having extensively studied to solve the above problems, that a varying polyether-modified polysiloxane can be highly refined by hydrogenation with a hydrogen gas in the presence of a catalyst and subsequent treatment in the presence of a solid acid to produce a deodorized, polyether-modified polysiloxane composition not producing a substance giving off a foul odor which results from hydrolysis, oxidation or the like of a by-product or unreacted material, and temporarily stable. They have investigated these findings to reach the present invention.

The first aspect of the present invention is a deodorized, polyether-modified polysiloxane composition, wherein a polyether-modified polysiloxane composition, synthesized by hydrosilylation in which a polyoxyalkylene having the carbon-carbon double bond at the terminal is reacted with an organohydrogen polysiloxane, is refined in the presence of a solid acid.

The second aspect of the present invention is the deodorized, polyether-modified polysiloxane composition of the first aspect, wherein the polyether-modified polysiloxane composition is refined by hydrogenation, in addition to treatment in the presence of a solid acid.

The third aspect of the present invention is the deodorized, polyether-modified polysiloxane composition of the second aspect, wherein the polyether-modified polysiloxane composition is refined first by hydrogenation and then by treatment in the presence of a solid acid.

The fourth aspect of the present invention is the deodorized, polyether-modified polysiloxane composition of the second aspect, wherein the polyether-modified polysiloxane composition is refined first by treatment in the presence of a solid acid and then by hydrogenation.

The fifth aspect of the present invention is the deodorized, polyether-modified polysiloxane composition of the first aspect, wherein water is incorporated in the treatment in the presence of a solid acid.

The sixth aspect of the present invention is the deodorized, polyether-modified polysiloxane composition of the first aspect, wherein a lighter fraction is distilled off during or after the treatment in the presence of a solid acid, or during or after the treatment by hydrogenation.

The seventh aspect of the present invention is the deodorized, polyether-modified polysiloxane composition of the first aspect, wherein the solid acid is at least one selected from the group consisting of solid, acidic zirconium oxide, strongly acidic cation-exchanging resin, fluorinated sulfonic acid resin, acidic clay, alumina, silica-alumina and zeolite.

The eighth aspect of the present invention is the deodorized, polyether-modified polysiloxane composition of the seventh aspect, wherein the solid acid is one of solid, acidic zirconium oxide and strongly acidic cation-exchanging resin.

The ninth aspect of the present invention is the deodorized, polyether-modified polysiloxane composition of the eighth aspect, wherein the solid acid is solid, acidic zirconium oxide.

The tenth aspect of the present invention is the deodorized, polyether-modified polysiloxane composition of the seventh aspect, wherein the solid, acidic zirconium oxide is produced by a process involving kneading aluminum hydroxide and/or hydrous oxide, zirconium hydroxide and/or hydrous oxide, and a compound containing sulfuric acid, forming the above mixture, and firing the formed product at a temperature at which zirconia of the tetragonal structure is produced.

The 11$^{th}$ aspect of the present invention is the deodorized, polyether-modified polysiloxane composition of the first aspect, wherein the polyether-modified polysiloxane composition contains at least one selected from the group consisting of a compound represented by the general formula (1):

$$R^1{}_3SiO(R_2SiO)_m(RXSiO)_nSiR^1{}_3 \quad (1)$$

(wherein, Rs are each hydrogen atom, or a substituted or unsubstituted monovalent hydrocarbon group; "m" is 0 or a positive integer and "n" is 0 or a positive integer; and X is a group represented by the general formula:

$$—C_xH_{2x}(OC_2H_4)_y(OC_3H_6)_zOA$$
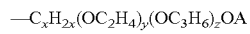

(wherein, A is hydrogen atom, or a group selected from the group consisting of a monovalent hydrocarbon group or one represented by the formula R$^2$—(CO)— (R$^2$ is a monovalent hydrocarbon group); "x" is an integer of 2 to 15, "y" is an integer of 0 to 100 and "z" is an integer of 0 to 100, "y+z" being an integer of 100 or less; and R$^1$ is a group selected from the group consisting of R and X, at least one of R$^1$s being X when "n" is 0), and the general formula (2):

$$[(R_2SiO)_mR_2SiC_xH_{2x}(OC_2H_4)_y(OC_3H_6)_zOC_xH_{2x}]_p \quad (2)$$
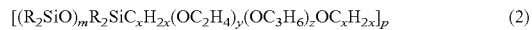

(wherein, Rs are each hydrogen atom, or a substituted or unsubstituted monovalent hydrocarbon group; "m" is a positive integer and "p" is an integer of 1 to 100, "x" is an integer of 2 to 15, "y" is an integer of 0 to 100 and "z" is an integer of 0 to 100, "y+z" being an integer of 100 or less).

The 12$^{th}$ aspect of the present invention is the deodorized, polyether-modified polysiloxane composition of the first aspect, wherein an antioxidant is incorporated.

The 13$^{th}$ aspect of the present invention is a method for producing a deodorized, polyether-modified polysiloxane composition, comprising a step of treating a polyether-modified polysiloxane composition, synthesized by hydrosilylation in which a polyoxyalkylene having the carbon-carbon double bond at the terminal is reacted with an organohydrogen polysiloxane, in the presence of a solid acid.

The 14$^{th}$ aspect of the present invention is the method of the 13$^{th}$ aspect for producing a deodorized, polyether-modified polysiloxane composition, comprising a step of hydrogenation of the polyether-modified polysiloxane composition, in addition to the treatment in the presence of a solid acid.

The 15$^{th}$ aspect of the present invention is the method of the 14$^{th}$ aspect for producing a deodorized, polyether-modified polysiloxane composition, wherein the treatment in the presence of a solid acid is carried out before or after the hydrogenation of the polyether-modified polysiloxane composition.

The 16$^{th}$ aspect of the present invention is the method of the 13$^{th}$ aspect for producing a deodorized, polyether-modified polysiloxane composition, wherein a step for distilling off a lighter fraction is carried out during or after the treatment in the presence of a solid acid, or before or after the treatment by hydrogenation.

The 17$^{th}$ aspect of the present invention is the method of the 13$^{th}$ aspect for producing a deodorized, polyether-modified polysiloxane composition, wherein the solid acid is at least one selected from the group consisting of solid, acidic zirconium oxide, strongly acidic cation-exchanging resin, fluorinated sulfonic acid resin, acidic clay, alumina, silica-alumina and zeolite.

The 18$^{th}$ aspect of the present invention is the method of the 17$^{th}$ aspect for producing a deodorized, polyether-modified polysiloxane composition, wherein the solid acid is one of solid, acidic zirconium oxide and strongly acidic cation-exchanging resin.

The 19th aspect of the present invention is a cosmetic containing the deodorized, polyether-modified polysiloxane composition of one of the first to 12th aspects.

As described above, the present invention relates to a deodorized, polyether-modified polysiloxane composition, wherein a polyether-modified polysiloxane composition, synthesized by hydrosilylation in which a polyoxyalkylene having the carbon-carbon double bond at the terminal is reacted with an organohydrogen polysiloxane, is refined in the presence of a solid acid. Some of the preferred embodiments are described below.

(1) The deodorized, polyether-modified polysiloxane composition of the 11th aspect, wherein the polyether-modified polysiloxane composition is represented by the general formula (2).

(2) The method of the 13th aspect for producing a deodorized, polyether-modified polysiloxane composition, wherein water is incorporated in the treatment in the presence of a solid acid.

(3) The method of the 15th aspect for producing a deodorized, polyether-modified polysiloxane composition, wherein the treatment in the presence of a solid acid is carried out after the hydrogenation of the polyether-modified polysiloxane composition.

(4) The method of the 15th aspect for producing a deodorized, polyether-modified polysiloxane composition, wherein the treatment in the presence of a solid acid is carried out before the hydrogenation of the polyether-modified polysiloxane composition.

(5) The method of the 18th aspect for producing a deodorized, polyether-modified polysiloxane composition, wherein the solid acid is solid, acidic zirconium oxide.

(6) The method of the 18th aspect for producing a deodorized, polyether-modified polysiloxane composition, wherein the solid acid is strongly acidic cation-exchanging resin.

DETAILED DESCRIPTION OF THE INVENTION

The deodorized, polyether-modified polysiloxane composition, method for producing the same and cosmetic containing the same of the present invention are described in more detail for each item.

The deodorized, polyether-modified polysiloxane composition of the present invention is a polyether-modified polysiloxane composition, synthesized by hydrosilylation in which a polyoxyalkylene having the carbon-carbon double bond at the terminal is reacted with an organohydrogen polysiloxane, refined in the presence of a solid acid.

1. Polyether-modified Polysiloxane Composition

The organohydrogen polysiloxanes for forming the polyether-modified polysiloxane composition for the present invention by hydrosilylation include a compound represented by the following formula:

$R^1{}_3SiO(R^1{}_2SiO)_nSiR^1{}_3$

[wherein, $R^1$s are each a substituted or unsubstituted monovalent hydrocarbon group (e.g., alkyl of 1 to 19 carbon atoms (e.g., methyl or ethyl), phenyl, alkylphenyl, naphthyl, alkylnaphthyl or phenylalkyl group, or 3-aminopropyl, 3-(N-2-aminoethylamino)propyl or 3,3,3-trifluoropropyl group, which may be the same or different, group represented by the following formula:

$-O-(R^2{}_2SiO)_qSiR^2{}_3$

[wherein, $R^2$s are each a substituted or unsubstituted monovalent hydrocarbon group (e.g., alkyl (e.g., methyl or ethyl), phenyl, alkylphenyl or phenylalkyl group of 1 to 19 carbon atoms, or 3-aminopropyl, 3-(N-2-aminoethylamino)propyl or 3,3,3-trifluoropropyl group, which may be the same or different, or hydrogen atom; and "q" is 0 or a positive integer], or hydrogen atom; and "n" is 0 or positive integer, where there is at least one hydrogen atom directly bound to the silicon atom in the molecule, or group represented by the following formula:

$[-(R_2{}^1SiO)_m-]$ (wherein, $R^1$ is the same as the above; and "m" is an integer of 3 or more, where there is at least one hydrogen atom directly bound to the silicon atom in the molecule].

These organohydrogen polysiloxanes may be used either individually or in combination.

The polyoxyalkylenes for forming the polyether-modified polysiloxane composition by hydrosilylation include a compound represented by the following formula:

$R'O(R''O)_xR'$

[wherein, R's are each a substituted or unsubstituted monovalent unsaturated hydrocarbon group (e.g., allyl, methallyl or 3-butenyl group, or an alkyl, phenyl, alkylphenyl, naphthyl or alkylnaphthyl of 1 to 19 carbon atoms), acyl group or hydrogen atom, which may be the same or different; R''s are each a substituted or unsubstituted divalent hydrocarbon group (e.g., ethylene, propylene or butylenes); and "x" is 0 or positive integer, where at least one R' in the molecule is a hydrocarbon group having an unsaturated substituent].

These polyoxyalkylenes may be used either individually or in combination.

The hydrosilylation can be carried out by a known process. For example, it may be carried out in the presence or absence of solvent, and the solvent, when used, may be selected from organic solvents, e.g., the one based on alcohol (e.g., ethanol or isopropyl alcohol), aromatic hydrocarbon (toluene or xylene), ether (e.g., dioxane or THF), aliphatic hydrocarbon and chlorinated hydrocarbon.

The hydrosilylation may be carried out in the absence of catalyst, but preferably in the presence of catalyst to reduce reaction temperature and/or reaction time. The hydrosilylation catalysts useful for the present invention include platinum, ruthenium, rhodium, palladium, osmium and iridium compounds, of which platinum compounds are particularly preferable for their high catalytic activity. The platinum compounds include chloroplatinate; metallic platinum; metallic platinum carried by alumina, silica, carbon black or the like; and platinum complexes, e.g., platinum/vinyl siloxane, platinum/phosphine and platinum/alcolate. The platinum catalyst, when used, is incorporated in the system at 0.0001 to 0.1% by weight as metallic platinum.

The hydrosilylation is normally carried out at 50 to 150° C. for 10 minutes to 24 hours, preferably 1 to 10 hours.

The reaction system normally contains an excessive quantity of the polyoxyalkylene.

The examples of the polyether-modified polysiloxane composition produced by the hydrosilylation include those represented by the general formula (1):

$$R^1_3SiO(R_2SiO)_m(RXSiO)_nSiR^1_3 \quad (1)$$

(wherein, Rs are each hydrogen atom, or a substituted or unsubstituted monovalent hydrocarbon group; "m" is 0 or a positive integer and "n" is 0 or a positive integer; and X is a group represented by the general formula:

$$-C_xH_{2x}(OC_2H_4)_y(OC_3H_6)_zOA$$

(wherein, A is hydrogen atom, or a group selected from the group consisting of a monovalent hydrocarbon group or one represented by the formula $R^2-(CO)-$ ($R^2$ is a monovalent hydrocarbon group); "x" is an integer of 2 to 15, "y" is an integer of 0 to 100 and "z" is an integer of 0 to 100, "y+z" being an integer of 100 or less; and $R^1$ is a group selected from the group consisting of R and X, at least one of $R^1$s being X when "n" is 0), or the general formula (2):

$$[(R_2SiO)_mR_2SiC_xH_{2x}(OC_2H_4)_y(OC_3H_6)_zOC_xH_{2x}]_p \quad (2)$$

(wherein, Rs are each hydrogen atom, or a substituted or unsubstituted monovalent hydrocarbon group; "m" is a positive integer and "p" is an integer of 1 to 100, "x" is an integer of 2 to 15, "y" is an integer of 0 to 100 and "z" is an integer of 0 to 100, "y+z" being an integer of 100 or less).

2. Refining of the Polyether-modified Polysiloxane Composition

The normal polyether-modified polysiloxane composition is refined by distilling off the solvent from the hydrosilylation effluent. Therefore, the unreacted polyoxyalkylene remains in the polyether-modified polysiloxane composition. An allyl-etherified polyoxyalkylene may cause isomerization in the presence of a catalyst, e.g., platinum catalyst. For example, hydrosilylation of a polyoxyalkylene allyl-etherified at the terminal produces a propenyl-etherified polyoxyalkylene at a constant rate. As a result, a propenyl-etherified polyoxyalkylene and polyoxyalkylene allyl-etherified at the terminal remain in the polyether-modified polysiloxane composition contains.

The propenyl-etherified polyoxyalkylene is a vinyl ether type compound, and is easily hydrolyzed to produce a lighter product. In other words, the propenyl-etherified polyoxyalkylene is gradually hydrolyzed in the presence of moisture in air and only a small quantity of acid to produce propionaldehyde, which gives off a foul odor.

An unreacted polyoxyalkylene allyl-etherified at the terminal is gradually transformed into the propenyl-etherified polyoxyalkylene by the action of a platinum catalyst remaining in the polyether-modified polysiloxane composition or deteriorated by oxidation proceeding with the lapse of time, to give off a foul odor. Moreover, a polyoxyalkylene allyl-etherified at the terminal is itself less stable to oxidation than a normal saturated hydrocarbon, and the resulting oxide can cause a foul odor. When a vinyl silane type compound is produced as a by-product of the hydrosilylation, it is considered to be low in stability to oxidation. It is therefore necessary to remove a propenyl-etherified polyoxyalkylene and, at the same time, not to allow a compound structurally unstable to cause a foul odor to remain in the polyether-modified polysiloxane composition, in order to produce the composition stable with time to cause no foul odor by hydrolysis or oxidation.

The deodorized, polyether-modified polysiloxane composition of the present invention is a polyether-modified polysiloxane composition, synthesized by hydrosilylation, refined in the presence of a solid acid. The refining process preferably includes treatment by the hydrogenation described below. When coupled with the hydrogenation, the treatment in the presence of a solid acid refines the polyether-modified polysiloxane composition to a still higher extent.

The treatment in the presence of a solid acid may come before or after the hydrogenation.

(1) Treatment by Hydrogenation

First, the treatment by hydrogenation is described.

The treatment by hydrogenation is carried out to hydrogenate a compound having an unsaturated substituent, e.g., carbon-carbon double bond, and compound produced by hydrolysis or oxidation, and thereby to produce the refined polyether-modified polysiloxane composition.

A known hydrogenation catalyst, e.g., nickel, palladium, platinum, rhodium, cobalt, chromium, copper or iron in the form of element or compound is used for the treatment. The catalyst carrier is not essential. When used, it is of activated carbon, silica, silica-alumina, alumina, zeolite or the like. The platinum catalyst for the hydrosilylation can be directly used. These catalysts may be used either individually or in combination.

The hydrosilylation can be carried out in the presence or absence of solvent, and the solvent, when used, may be selected from those unreactive under the hydrogenation conditions, e.g., the one based on alcohol (e.g., ethanol or isopropyl alcohol), aromatic hydrocarbon (toluene or xylene), ether (e.g., dioxane or THF), aliphatic hydrocarbon, chlorinated hydrocarbon and water. The solvent for the hydrosilylation can be directly used. These solvents may be used either individually or in combination.

The hydrogenation may be carried out at normal or elevated pressure, in actuality at an elevated pressure of 1 to 200 Kg/cm² in a hydrogen atmosphere. Hydrogenation temperature is 0 to 200° C., preferably 50 to 170° C. to shorten reaction time.

The hydrogenation process may be batchwise or continuous. For the batchwise process, reaction time is around 3 to 12 hours, although varying depending on conditions, e.g., catalyst quantity and temperature.

In the batchwise process, the hydrogenation reaction may be terminated 1 to 2 hours after the hydrogen pressure shows essentially no decrease. However, it is preferable to keep pressure at a high level by making up hydrogen for shortening reaction time, when it decreases during the reaction process.

The hydrogenation effluent is filtered by diatomaceous earth or activated carbon under a pressure with nitrogen, to separate the catalyst for the hydrosilylation and hydrogenation.

When a solvent is used for the reaction, or a lighter fraction is present in the hydrogenation effluent, the polyether-modified polysiloxane composition is refined by distilling off the solvent or lighter fraction, as required, under a vacuum in an atmosphere of nitrogen blown into the system. Removal of the lighter fraction may be carried out as a pretreatment step for the hydrogenation, or twice before and after the hydrogenation.

The hydrogenation treatment can deodorize the polyether-modified polysiloxane composition to some extent, because it removes the unsaturated group from the composition and hence reduces propionaldehyde or the like derived from the unsaturated group.

However, the hydrogenation treatment alone may allow an aldehyde condensate, e.g., acetal, to remain in the composition, as discussed above. It may be transformed into aldehyde in an aqueous solution to cause a foul odor. This is because the hydrogenation treatment alone cannot remove an aldehyde condensate, which contains no unsaturated bond, and hence a substance which causes a foul odor will still remain in the hydrogenation effluent.

(2) Treatment in the Presence of a Solid Acid

The present invention treats the polyether-modified siloxane composition in the presence of a solid acid in combination with the treatment by hydrogenation described above, which cannot completely remove an aldehyde condensate, e.g., acetal. The treatment in the presence of a solid acid can deodorize the composition by decomposing the aldehyde condensate remaining therein, i.e., can produce a deodorized polyether-modified siloxane composition.

As described above, the treatment in the presence of a solid acid may come before the hydrogenation. In this case, a propenyl-etherified polyoxyalkylene and aldehyde condensate, e.g., acetal, are decomposed in the presence of a solid acid, and the aldehyde produced, residual alkenylated polyoxyalkylene and the like are reduced by the hydrogenation. This process can also deodorize the polyether-modified siloxane composition.

Moreover, the present invention can depend only on the treatment in the presence of a solid acid, which can decompose an aldehyde condensate, e.g., acetal, in addition to a propenyl-etherified polyoxyalkylene, as discussed above, and hence deodorize the polyether-modified siloxane composition.

The treatment in the presence of a solid acid for the present invention means a decomposition treatment in which the polyether-modified siloxane composition synthesized by the hydrosilylation is stirred together with a solid acid in a reaction system (e.g., flask or other reactors), or hydrolysis treatment in which it is stirred together with a solid acid and water or solid acid, water and organic solvent, although not limited thereto. The hydrolysis treatment with stirring in the presence of a solid acid and water is particularly preferable. It is preferably carried out under the conditions of 0 to 200° C., more preferably 80 to 100° C., for around 0.5 to 24 hours, more preferably 1 to 10 hours.

Alternately, the polyether-modified siloxane composition synthesized by the hydrosilylation may be passed (flown) in a reactor packed with a solid acid. In this case, the reaction is carried out at 0 to 200° C., preferably 80 to 100° C., for around 0.5 to 24 hours, preferably around 1 to 10 hours, with recycling.

When a lighter fraction is present in the reaction system, it is preferable to refine the polyether-modified polysiloxane composition by distilling off the lighter fraction, as required, under a vacuum in an atmosphere of nitrogen blown into the system while the composition is treated in the presence of a solid acid. Removal of the lighter fraction may be carried out as a pretreatment or post treatment step for the treatment in the presence of a solid acid, or twice before and after the treatment in the presence of a solid acid.

In the present invention, the treatment in the presence of a solid acid can be preferably carried out in the presence of water, as discussed above. A water-soluble organic solvent may be used in combination with water, when the polyether-modified polysiloxane composition is sparingly soluble in water. The organic solvents useful for the present invention include a saturated, monovalent alcohol of 1 to 5 carbon atoms, THF, dioxane and acetone.

The solid acid is an acidic solid. The present invention uses at least one type of a solid acid selected from the group consisting of solid, acidic zirconium oxide (or solid, acidic zirconia), strongly acidic cation-exchanging resin, fluorinated sulfonic acid resin, acidic clay, alumina, silica-alumina and zeolite. It is preferably solid, acidic zirconium oxide or strongly acidic cation-exchanging resin, the former being more preferable.

More specifically, the solid, acidic zirconium oxide is prepared by treating zirconium hydroxide with sulfuric acid and then heating at 300° C. or higher. Still more specifically, the solid, acidic zirconium oxide, e.g., zirconia sulfate, can be prepared by a process comprising steps of kneading aluminum hydroxide and/or hydrous oxide, zirconium hydroxide and/or hydrous oxide and a compound containing sulfuric acid; forming the above mixture; and firing the formed product at a temperature, more specifically 300° C. or higher, at which zirconia of the tetragonal structure is produced. The commercial products include "SZA-60" supplied by Japan Energy as a solid, acidic zirconium catalyst.

The strongly acidic cation-exchanging resins include the one having a sulfonic acid group ($-SO_3H$) as a functional group. The commercial products include Amberlists 15, 16, 31 and 35 (US's Rhom and Haas, supplied by Organo). The fluorinated sulfonic acid resin is a perfluorinated polymer having a sulfonic acid group bound to and suspended from the polymer chain. It is specifically disclosed by, e.g., JP-B-59-4446.

The treatment in the presence of a solid acid allows no acid to remain in the system. It disperses with a neutralization step, and allows no neutralization salt to remain in the system. When treated in the presence of a solid acid, therefore, the polyether-modified polysiloxane composition is free from deterioration resulting from a residual acidic substance or neutralization salt with the lapse of time, more specifically resulting from oxidation of the composition in the presence of a residual acid, or depolymerization or polymerization of the composition in the presence of a residual neutralization salt. The composition containing no residual acid or neutralization salt has another advantage that the hydrogenation reaction, when carried out after the treatment in the presence of a solid acid, is not retarded by the residual acid or salt. Still another advantage is that the composition gives off no foul odor caused by the residual acid or salt by itself or its decomposition.

The deodorized, polyether-modified polysiloxane composition may be incorporated, after being refined, with an antioxidant, e.g., one based on phenol, hydroquinone, benzoquinone, aromatic amine or vitamin, to have improved stability against oxidation.

The antioxidants useful for the present invention include 2,6-di-t-butyl-p-cresol (BHT), and vitamins C and E. It is incorporated at 10 to 1000 ppm based on the deodorized, polyether-modified polysiloxane composition after it is refined, preferably 50 to 500 ppm.

It may be incorporated before the step of distilling off the lighter fraction.

The deodorized, polyether-modified polysiloxane composition of the present invention can be used for various purposes. In particular, it can go into cosmetics, centered by the perfume-free ones for the skin and hair, for which the conventional polyether-modified polysiloxane composition is difficult to use for its foul odor.

When used for a cosmetic, the deodorized, polyether-modified polysiloxane composition of the present invention is incorporated preferably at around 0.1 to 40% by weight based on the whole cosmetic. Moreover, it may be incorporated with any known component normally used for cosmetics within limits not harmful to the effect of the present invention.

For hair cosmetics, for example, it may be incorporated with any known component normally used within limits not harmful to the effect of the present invention. More specifically, these components include silicone compounds in the form of oil, resin, gum, rubber, powder or the like [e.g., dimethyl polysiloxane, dimethyl methylphenyl polysiloxane, amino-modified dimethyl polysiloxane, epoxy-modified dimethyl polysiloxane and polycaprolactone-modified dimethyl polysiloxane]; various oils [camellia oil, rapeseed oil, sesame oil, safflower oil, cotton oil, castor oil, soybean oil, copra oil, palm oil, beeswax, montan wax, lanoline and squalene]; surfactants [e.g., alkyl benzene sulfonate, polyoxyalkylene alkyl benzene sulfuric acid ester, alkyl sulfuric acid ester, alkane sulfonate, alkyl ethoxy carboxylate, succinic acid derivative, alkyl amine oxide, imidazoline type compound, polyoxyethylene alkyl or alkenyl ether, polyoxyethylene alkylphenyl ether, and higher fatty acid alkanol amide and alkylene oxide adduct thereof]; high-molecular-weight compounds [e.g., hydroxyethyl cellulose, hydroxypropyl cellulose, hydroxypropylmethyl cellulose, methyl cellulose, cationized cellulose, cationized high-molecular-weight compound, polyvinyl pyrrolidone, vinyl pyrrolidone/vinyl acetate copolymer, vinyl pyrrolidone/vinyl acetate/alkylaminoacrylate copolymer, lower alkyl half-ester of methylvinyl ether/maleic anhydride copolymer, vinyl acetate/crotonic acid copolymer, acrylic acid/acrylic acid ester/N-alkyl acrylamide copolymer, vinyl acetate/crotonic acid/vinyl-tert-butyl benzoate copolymer, poly(2-acrylamide-2-sodium methyl propane sulfonate), vinyl pyrrolidone/methacrylic acid/acetic acid (tert-butyl) copolymer and vinyl pyrrolidone/acrylic acid (or methacrylic acid) copolymer; amino acids [e.g., glycine, serine and proline]; powders [e.g., sericite, silica-alumina, silica gel, kaolin, talc, colcothar, ultramarine blue, mica, mica titanium, iron oxide, titanium oxide, magnesium oxide, chromium oxide, antimony oxide, zinc monoxide, zinc dioxide, magnesium carbonate, calcium carbonate, calcium phosphate, barium sulfate, aluminum hydroxide, chromium hydroxide, magnesium aluminometasilicate, magnesium aluminosilicate and polyethylene]; and antioxidants, ultraviolet absorbers, humectants, perfumes, dyes, pigments, colorants, preservatives, vitamin preparations, hormone preparations, deodorants, sticking agents and anti-inflammatory agents.

EXAMPLES

The present invention is described by EXAMPLES and COMPARATIVE EXAMPLES, which by no means limit the present invention.

Example 1

Synthesis and Refining Polyether-modified Polysiloxane 1

A 1000 mL (1 L) four-mouthed flask equipped with a stirrer, reflux condenser, thermometer and nitrogen inlet port was charged with 240 g of methyl hydrogen polysiloxane (hydrogen generation rate: 93.51 mL/g, structural formula: $(CH_3)_3SiO[(CH_3)_2SiO]_{10}[(CH_3)HSiO]_5Si(CH_3)_3$ and 666.7 g of allyl polyether (structural formula: $CH_2=CHCH_2O(C_2H_4O)_{10}CH_3$, to which a toluene solution of platinum divinyltetramethyl disiloxane (platinum concentration: 3.0% by weight) was added for the reaction at 80° C. for 2 hours.

The effluent was hydrolyzed at 95° C. for 5 hours in the presence of 1.3 g of zirconia sulfate (Japan Energy, SZA-60) and 9 g of refined water. The effluent was treated by vacuum distillation to remove the lighter fraction and then by filtration to prepare Polyether-modified Polysiloxane 1.

Polyether-modified Polysiloxane 1 is structurally represented by the general formula (1), wherein $R=R^1=A=CH_3$, "m"=10, "n"=5, "x"=3, "y"=10 and "z"=0, i.e., $(CH_3)_3SiO[(CH_3)_2SiO]_{10}[(CH_3)(C_3H_6O(C_2H_4O)_{10}CH_3)SiO]_5Si(CH_3)_3$.

Example 2

Polyether-modified Polysiloxane 2

In this example, 700 g of Polyether-modified Polysiloxane 1 prepared in EXAMPLE 1 was hydrogenated in an autoclave with hydrogen at 140° C. and 80 kg/cm² for 6 hours in the presence of 35 g of Raney nickel. The effluent was treated by filtration to remove the catalyst, by vacuum distillation to remove the lighter fraction and then by filtration to prepare Polyether-modified Polysiloxane 2.

Example 3

Synthesis and Refining Polyether-modified Polysiloxane 3

A 1 L four-mouthed flask equipped with a stirrer, reflux condenser, thermometer and nitrogen inlet port was charged with 240 g of methyl hydrogen polysiloxane (hydrogen generation rate: 93.51 mL/g, structural formula: $(CH_3)_3SiO[(CH_3)_2SiO]_{10}[(CH_3)HSiO]_5Si(CH_3)_3$ and 666.7 g of allyl polyether (structural formula: $CH_2=CHCH_2O(C_2H_4O)_{10}CH_3$, to which a 10% ethanol solution of chloroplatinic acid was added for the reaction at 80 to 100° C. for 2 hours.

The effluent was neutralized with sodium bicarbonate, and treated by vacuum distillation at 90 to 100° C. to remove the lighter fraction and then by filtration.

In this example, 700 g of the filtrate prepared above was hydrogenated in an autoclave with hydrogen at 140° C. and 80 kg/cm² for 6 hours in the presence of 35 g of Raney nickel. The effluent was treated by filtration to remove the catalyst, hydrolyzed at 95° C. for 5 hours in the presence of 1 g of zirconia sulfate (Japan Energy, SZA-60) and 6 g of refined water. The effluent was treated by vacuum distillation to remove the lighter fraction and then by filtration to prepare Polyether-modified Polysiloxane 3.

Polyether-modified Polysiloxane 3 was structurally the same as Polyether-modified Polysiloxane 1.

Example 4

Synthesis and Refining Polyether-modified Polysiloxane 4

A 1 L four-mouthed flask equipped with a stirrer, reflux condenser, thermometer and nitrogen inlet port was charged with 240 g of methyl hydrogen polysiloxane (hydrogen generation rate: 93.51 mL/g, structural formula: $(CH_3)_3SiO[(CH_3)_2SiO]_{10}[(CH_3)HSiO]_5Si(CH_3)_3$ and 666.7 g of allyl polyether (structural formula: $CH_2=CHCH_2O(C_2H_4O)_{10}CH_3$, to which a 10% ethanol solution of chloroplatinic acid was added for the reaction at 80 to 100° C. for 2 hours.

The effluent was neutralized with sodium bicarbonate, and treated by vacuum distillation at 90 to 100° C. to remove the lighter fraction and then by filtration.

In this example, 700 g of the filtrate prepared above was hydrogenated in an autoclave with hydrogen at 140° C. and 80 kg/cm² for 6 hours in the presence of 35 g of Raney nickel. The effluent was treated by filtration to remove the catalyst.

The filtrate was also hydrolyzed by another flow system comprising a pump, reactor tower (inner diameter: 15 mm) equipped with a furnace and 500 mL, four-mouthed flask equipped with a magnetic stirrer connected in this order, where the reactor tower was packed with 20 mL of zirconia sulfate (Japan Energy, SZA-60) and sealed with glass wool at both ends. The zirconia sulfate was moderately crushed by a mortar beforehand to have a uniform size of 10 to 20 meshes and fired at 350° C. for 2 hours in an oven immediately before the test.

A mixture of 300 mL of the filtrate prepared above and 3 g of refined water, put in the four-mouthed flask, was flown with stirring through the reaction system kept at 100° C. for 6 hours, where the effluent was treated by vacuum distillation to remove the lower-boiling-point fraction and then recycled back to the reactor tower to prepare Polyether-modified Polysiloxane 4.

Polyether-modified Polysiloxane 4 was structurally the same as Polyether-modified Polysiloxane 1.

Example 5

Polyether-modified Polysiloxane 5

Polyether-modified Polysiloxane 5 was prepared in the same manner as in EXAMPLE 3, except that zirconia sulfate was replaced by a strongly acidic cation-exchanging resin (Organo, Amberlist 35).

Comparative Example 1

Comparative Sample 1 was prepared in the same manner as in EXAMPLE 1, except that the effluent was not treated with zirconia sulfate, and treated by vacuum distillation, after it was incorporated with 2.5 g of sodium bicarbonate, to remove the lighter fraction and then by filtration.

Comparative Example 2

Comparative Sample 2 was prepared in the same manner as in EXAMPLE 1, except that the effluent was hydrolyzed with 9 g of 0.1 mols/L hydrochloric acid in place of zirconia sulfate at 95° C. for 1 hour, and treated by vacuum distillation, after it was incorporated with 4.5 g of sodium bicarbonate for neutralization, to remove the lighter fraction and then by filtration.

Comparative Example 3

Comparative Sample 3 was prepared in the same manner as in EXAMPLE 2, except that the effluent was not treated with zirconia sulfate.

Comparative Example 4

In this comparative example, 700 g of Comparative Sample 1 prepared in COMPARATIVE EXAMPLE 1 was hydrogenated in an autoclave with hydrogen at 140° C. and 80 kg/cm$^2$ for 6 hours in the presence of 35 g of Raney nickel, after it was incorporated with 3.5 g of a phosphoric acid-based buffer solution comprising phosphoric acid, citric acid and sodium hydroxide, adjusted at a pH of 3.3. The effluent was treated by filtration to remove the catalyst, by vacuum distillation to remove the lighter fraction and then by filtration to prepare Comparative Sample 4.

Comparative Example 5

Comparative Sample 5 was prepared in the same manner as in EXAMPLE 3, except that the effluent was hydrolyzed with 7 g of 0.1 mols/L hydrochloric acid in place of zirconia sulfate at 95° C. for 1 hour, and treated by vacuum distillation, after it was neutralized with 3.5 g of sodium bicarbonate, to remove the lighter fraction and then by filtration.

Comparative Example 6

In this comparative example, 700 g of Comparative Sample 2 prepared in COMPARATIVE EXAMPLE 2 was hydrogenated in an autoclave with hydrogen at 140° C. and 80 kg/cm$^2$ for 6 hours in the presence of 35 g of Raney nickel, as was the case with EXAMPLE 2. The effluent was treated by filtration to remove the catalyst, by vacuum distillation to remove the lighter fraction and then by filtration to prepare Comparative Sample 6.

The polyether-modified polysiloxanes prepared in EXAMPLES 1 to 5 and COMPARATIVE EXAMPLES 1 to 6 were evaluated for their odor, and changed viscosity and pH level.

For evaluation of the odor, the sample itself was observed immediately after it was prepared and after it was kept at 70° C. for 1 month. At the same time, a mixture of 3 g of the sample, 3 g of propylene glycol and 24 g of refined water was also observed immediately after it was prepared and after it was kept at 70° C. for 2 weeks for evaluating the compounded system.

They were evaluated according to the following standards:
No odor is given off. ◎
Little odor is given off. ○
Odor is given off slightly. Δ
Odor is given off strongly. ×

For evaluation of changed viscosity, the sample was observed immediately after it was prepared and after it was kept at 70° C. for 1 month.

For evaluation of changed pH level, the sample was observed immediately after it was prepared and after it was kept at 25° C. for 1 month, where it was dissolved in refined water to be tested at 25° C. as a 10% by weight aqueous solution.

The results are summarized in Table 1. As shown, it was confirmed that the deodorized, polyether-modified polysiloxane composition (polyether-modified polysiloxane) of the present invention has notable effects with respect to odor, and changed viscosity and pH level.

TABLE 1

| EXAMPLES/ COMPARATIVE EXAMPLES | Refining treatment | Odor | | | | Changed viscosity Change rate (%) | Changed pH level | |
|---|---|---|---|---|---|---|---|---|
| | | Sample itself | | Compounded system | | | pH | |
| | | Initial stage | After elapse of specific time | Initial stage | After elapse of specific time | | Initial stage | After elapse of specific time |
| EXAMPLE 1 | Solid acid (zirconia sulfate) | ◎ | ○ | ◎ | ○~Δ | Less than 1% | 6.8 | 6.3 |
| EXAMPLE 2 | Solid acid and hydrogenation | ◎ | ◎ | ◎ | ◎ | Less than 1% | 7.0 | 6.8 |

TABLE 1-continued

| EXAMPLES/ COMPARATIVE EXAMPLES | Refining treatment | Odor | | | | Changed viscosity Change rate (%) | Changed pH level | |
|---|---|---|---|---|---|---|---|---|
| | | Sample itself | | Compounded system | | | pH | |
| | | Initial stage | After elapse of specific time | Initial stage | After elapse of specific time | | Initial stage | After elapse of specific time |
| EXAMPLE 3 | Hydrogenation and solid acid | ◎ | ◎ | ◎ | ◎ | Less than 1% | 6.8 | 6.5 |
| EXAMPLE 4 | Fixed bed (zirconia sulfate) | ◎ | ◎ | ◎ | ◎ | Less than 1% | 6.9 | 6.5 |
| EXAMPLE 5 | Strongly acidic, cation-exchanging resin | ◎ | ◎ | ◎ | ◎ | Less than 1% | 6.9 | 6.6 |
| COMPARATIVE EXAMPLE 1 | Blank | X | X | X | X | Increased by 5% | 5.9 | 4.3 |
| COMPARATIVE EXAMPLE 2 | Treatment with hydrochloric acid | Δ | X | Δ | X | Increased by 10% | 5.4 | 3.2 |
| COMPARATIVE EXAMPLE 3 | Hydrogenation only | ◎ | ○ | ◎ | Δ | Less than 1% | 6.9 | 6.4 |
| COMPARATIVE EXAMPLE 4 | Hydrogenation in the presence of a buffer solution of phosphoric acid | ○ | X | Δ | X | Increased by 7% | 5.8 | 4.8 |
| COMPARATIVE EXAMPLE 5 | Hydrogenation and treatment with hydrochloric acid | ◎ | ○ | ◎ | ○~Δ | Increased by 5% | 6.1 | 5.7 |
| COMPARATIVE EXAMPLE 6 | Treatment with hydrochloric acid and hydrogenation | ◎ | ○ | ◎ | ○~Δ | Increased by 3% | 6.3 | 5.3 |

The deodorized, polyether-modified polysiloxane composition of the present invention is of a polyether-modified polysiloxane composition, synthesized by hydrosilylation in which a polyoxyalkylene having the carbon-carbon double bond at the terminal is reacted with an organohydrogen polysiloxane, and is highly refined by treatment in the presence of a solid acid, exhibiting notable effects of not producing a substance giving off a foul odor, while being produced or stored, which results from hydrolysis, oxidation or the like of a by-product or unreacted material and of being temporarily stable.

Therefore, it can go into cosmetics, centered by the perfume-free ones for the skin and hair, for which the conventional polyether-modified polysiloxane composition is difficult to use for its foul odor.

What is claimed is:

1. A method for producing a deodorized, polyether-modified polysiloxane composition, comprising a step of treating a polyether-modified polysiloxane composition, synthesized by hydrosilylation in which a polyoxyalkylene having the carbon-carbon double bond at the terminal is reacted with an organohydrogen polysiloxane, in the presence of a solid acid, being a member selected from the group consisting of solid, acidic zirconium oxide, strongly acidic cation-exchanging resin, fluorinated sulfonic acid resin, and acidic clay, by combining the polysiloxane composition, said solid acid and one or more members selected from the group consisting of water and organic solvent.

2. The method according to claim 1 for producing a deodorized, polyether-modified polysiloxane composition, comprising a step of hydrogenation of the polyether-modified polysiloxane composition, in addition to the treatment in the presence of a solid acid.

3. The method according to claim 2 for producing a deodorized, polyether-modified polysiloxane composition, wherein the treatment in the presence of a solid acid is carried out before or after the hydrogenation of the polyether-modified polysiloxane composition.

4. The method according to claim 1 for producing a deodorized, polyether-modified polysiloxane composition, wherein a step for distilling off a lighter fraction is carried out during or after the treatment in the presence of a solid acid, or before or after the treatment by hydrogenation.

5. The method according to claim 1 for producing a deodorized, polyether-modified polysiloxane composition, wherein the solid acid is one of solid, acidic zirconium oxide and strongly acidic cation-exchanging resin.

6. The method according to claim 1 wherein the polyether-modified polysiloxane composition contains at least one selected from the group consisting of a compound represented by the general formula (1):

$$R^1{}_3SiO(R_2SiO)_m(RXSiO)_nSiR^1{}_3 \quad (1)$$

wherein, Rs are each hydrogen atom, or a substituted or unsubstituted monovalent hydrocarbon group; "m" is 0 or a positive integer and "n" is 0 or a positive integer; and X is a group represented by the general formula:

$$-C_xH_{2x}(OC_2H_4)_y(OC_3H_6)_zOA$$

wherein, A is hydrogen atom, or a group selected from the group consisting of a monovalent hydrocarbon group or one represented by the formula $R^2-(CO)-$ ($R^2$ is a monovalent hydrocarbon group; "X" is an integer of 2 to 15, "y" is an integer of 0 to 100 and "z" is an integer of 0 to 100, "y+z" being an integer of 100 or less; and R' is a group selected from the group consisting of R and X, at least one of R's being X when "n" is 0, and a compound represented by the general formula (2):

$$[(R_2SiO)_mR_2SiC_xH_{2x}(OC_2H_4)_y(OC_3H_6)_zOC_xH_{2x}]_p \quad (2)$$

wherein, Rs are each hydrogen atom, or a substituted or unsubstituted monovalent hydrocarbon group; "m" is a positive integer and "p" is an integer of 1 to 100, "x" is an integer of 2 to 15, "y" is an integer of 0 to 100 and "Z" is an integer of 0 to 100, "y+z" being an integer of 100 or less.

7. The method according to claim 1 for producing a deodorized, polyether-modified polysiloxane composition, wherein the treating is hydrolysis treating.

8. The method according to claim 7 for producing a deodorized, polyether-modified polysiloxane composition, wherein the hydrolysis treating is carried out under conditions of 0 to 200° C. for around 0.5 to 24 hours.

9. The method according to claim 7 for producing a deodorized, polyether-modified polysiloxane composition, wherein the hydrolysis treating is carried out under conditions of 80 to 100° C. for around 1 to 10 hours.

10. The method according to claim 1 for producing a deodorized, polyether-modified polysiloxane composition, wherein the organic solvents are selected from the group consisting of saturated, monovalent alcohol of 1 to 5 carbon atoms, THF, dioxane and acetone.

11. The method according to claim 1 for producing a deodorized, polyether-modified polysiloxane composition, further comprising the step of incorporating with an antioxidant selected from the group consisting of 2,6-di-t-butyl-p-cresol (BHT), vitamin C and vitamin E.

12. The method according to claim 11 for producing a deodorized, polyether-modified polysiloxane composition, wherein the antioxidant is incorporated at 10 to 1000 ppm based on the deodorized, polyether-modified polysiloxane composition after it is refined.

13. The method according to claim 11 for producing a deodorized, polyether-modified polysiloxane composition, wherein the antioxidant is incorporated at 50 to 500 ppm based on the deodorized, polyether-modified polysiloxane composition after it is refined.

* * * * *